US006800449B1

(12) United States Patent
Haynes et al.

(10) Patent No.: US 6,800,449 B1
(45) Date of Patent: Oct. 5, 2004

(54) HIGH THROUGHPUT FUNCTIONAL PROTEOMICS

(75) Inventors: Paul A. Haynes, Encinitas, CA (US); Nancy L. Andon, Cardiff by the Sea, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 10/197,625

(22) Filed: Jul. 15, 2002

Related U.S. Application Data (60) Provisional application No. 60/305,264, filed on Jul. 13, 2001.

(51) Int. Cl.[7] ............................................. G01N 33/53
(52) U.S. Cl. ...................... 435/7.8; 435/7.23; 435/7.2; 435/7.1; 436/178; 436/177; 436/173; 436/161; 530/361; 530/350; 536/1.11
(58) Field of Search ................................. 435/7.8, 7.23, 435/7.2, 7.1; 436/178, 177, 173, 161; 530/361, 350; 536/1.11

(56) References Cited

U.S. PATENT DOCUMENTS

| | | | |
|---|---|---|---|
| 3,997,298 A | 12/1976 | McLafferty et al. ....... 23/253 R |
| 4,701,419 A | 10/1987 | Morris ......................... 436/89 |
| 4,820,648 A | 4/1989 | Caprioli et al. ............... 436/89 |
| 5,130,538 A | 7/1992 | Fenn et al. .................. 250/282 |
| 5,210,412 A | 5/1993 | Levis et al. ................. 250/288 |
| 5,240,859 A | 8/1993 | Aebersold ..................... 436/89 |
| 5,432,093 A | 7/1995 | Bailey et al. .................. 436/89 |
| 5,470,753 A | 11/1995 | Sepetov et al. ............... 436/89 |
| 5,493,115 A | 2/1996 | Deinzer et al. ............. 250/281 |
| 5,510,240 A | 4/1996 | Lam et al. .................... 435/7.1 |
| 5,521,097 A | 5/1996 | Uchida et al. ................ 436/86 |
| 5,527,675 A | 6/1996 | Coull et al. ..................... 435/6 |
| 5,534,440 A | 7/1996 | Aebersold et al. ............ 436/89 |
| 5,538,897 A * | 7/1996 | Yates et al. ................... 436/89 |
| 5,595,636 A | 1/1997 | Franzen ....................... 204/464 |
| 5,607,859 A | 3/1997 | Biemann et al. ............. 436/173 |
| 5,608,217 A | 3/1997 | Franzen et al. .............. 250/288 |
| 5,614,368 A | 3/1997 | Ghazarossian et al. ...... 435/7.5 |
| 5,625,184 A | 4/1997 | Vestal et al. ................. 250/287 |
| 5,635,404 A | 6/1997 | Wilson ......................... 436/173 |
| 5,643,800 A | 7/1997 | Tarantino et al. ........... 436/518 |
| 5,658,739 A | 8/1997 | Woods, Jr. ................... 435/7.1 |
| 5,681,751 A | 10/1997 | Begg et al. ................... 436/89 |
| 5,734,161 A | 3/1998 | Koster ......................... 250/287 |
| 5,760,393 A | 6/1998 | Vestal et al. ................. 250/282 |
| 5,777,324 A | 7/1998 | Hillenkamp ................. 250/288 |
| 5,782,102 A | 7/1998 | Iritani et al. .................. 62/197 |
| 5,792,664 A | 8/1998 | Chait et al. ................... 436/89 |
| 5,807,748 A | 9/1998 | Bailey .......................... 436/89 |
| 5,808,300 A | 9/1998 | Caprioli ....................... 250/288 |
| 5,821,063 A | 10/1998 | Patterson et al. .............. 435/6 |
| 5,824,556 A | 10/1998 | Tarr ............................. 436/89 |
| 5,827,659 A | 10/1998 | Patterson ....................... 435/6 |
| 5,834,195 A | 11/1998 | Benkovic et al. .............. 435/6 |
| 5,869,240 A | 2/1999 | Patterson ....................... 435/6 |
| 5,872,015 A | 2/1999 | Venton et al. ............... 436/538 |
| 5,885,841 A | 3/1999 | Higgs, Jr. et al. ............. 436/89 |
| 5,906,747 A | 5/1999 | Coffman et al. ............. 210/635 |
| 5,917,185 A | 6/1999 | Yeung et al. ................ 250/288 |
| 5,952,653 A | 9/1999 | Covey et al. ................ 250/288 |
| 5,993,662 A | 11/1999 | Garr et al. ................... 210/656 |
| 6,017,693 A | 1/2000 | Yates, III et al. ............... 435/5 |
| 6,027,890 A | 2/2000 | Ness et al. ...................... 435/6 |
| 6,057,543 A | 5/2000 | Vestal et al. ................. 250/282 |
| 6,075,127 A | 6/2000 | Roggero et al. ............. 530/412 |
| 6,107,623 A | 8/2000 | Bateman et al. ............. 250/282 |
| 6,111,251 A | 8/2000 | Hillenkamp ................. 250/288 |
| 6,140,639 A | 10/2000 | Gusev et al. ................ 250/288 |
| 6,147,344 A | 11/2000 | Annis et al. ................. 250/281 |
| 6,156,527 A | 12/2000 | Schmidt et al. ............... 435/24 |
| 6,188,064 B1 | 2/2001 | Köster ......................... 250/282 |
| 6,203,990 B1 | 3/2001 | Fahy ............................. 435/6 |
| 6,207,370 B1 | 3/2001 | Little et al. .................... 435/6 |
| 6,214,561 B1 | 4/2001 | Peters et al. ................. 435/7.1 |
| 6,225,047 B1 | 5/2001 | Hutchens et al. .............. 435/5 |

FOREIGN PATENT DOCUMENTS

| | | | |
|---|---|---|---|
| WO | WO99/12040 | 3/1999 | .......... G01N/33/68 |
| WO | WO99/43409 | 9/1999 | .......... B01D/15/08 |
| WO | WO99/62930 | 12/1999 | |
| WO | WO0011208 | 3/2000 | .......... C12Q/1/00 |
| WO | WO00/29987 | 5/2000 | .......... G06F/17/30 |
| WO | WO00/33075 | 6/2000 | .......... G01N/33/53 |
| WO | WO00/63683 | 10/2000 | .......... G01N/27/26 |

OTHER PUBLICATIONS

Butt et al, Proteomics, 1, 42–53, (2001).*
Washburn et al, Nature Biotechnology, 19, 242–47 (Mar. 2001).*
Cai et al, Anal. Chem. 68, 72–78, (1996).*
Nedved et al, Anal. Chem. 68, 4228–36 (Dec. 1, 1996).*
Molloy et al, Eur. J. Biochem. 267, 2871–81 (2000).*
Cassar–Malek et al, V–ErbaA, an oncogene stimulating avian myoblast differentiation [abstract] HCAPLUS, copyright 2001 BIOSIS, Accession No. 1997:486940, Medicine Sciences, vol. 13, No. 8–9 (1997), pp. 952–960.
Huang et al, Splase: the design of a new restriction enzyme with specificity for Sp1 binding sites [abstract] HCAPLUS, copyright 2001 ACS, Accession No. 1997:287389, Perspectives in Protein Engineering '96, [Int. Conf.], 5th (1996), Paper No. 23, 24 pp.; Editor(s): Geisow, Michael J., (Biodigm, Bingham, UK).
Kuwahara, J., Coleman, J.E., Role of the Zinc–II Ions in the Structure of the Three–Finger DNA Binding Domain of the SP1 Transcription Factor [abstract] HCAPLUS, copyright 2001 Biosis, Accession No. 1997:517369, Biochemistry, vol. 29, No. 37 (1990), pp. 8627–8631.
Staby et al., "Comparison of chromatographic ion–exchange resins I. Strong anion–exchange resins", Journal of Chromatography, (2002), pp. 99–111.

* cited by examiner

Primary Examiner—T. D. Wessendorf
(74) Attorney, Agent, or Firm—Jenkins, Wilson & Taylor, P.A.

(57) ABSTRACT

A method is disclosed which provides a high throughput method for assigning plausible functions to unknown sequence entries in a particular database. The method was used herein to identify lectin proteins which can be found in specific tissues of the rice plant.

12 Claims, 4 Drawing Sheets

SEQUENCE LISTING

```
<160> NUMBER OF SEQ ID NOS: 5

<210> SEQ ID NO 1
<211> LENGTH: 16
<212> TYPE: PRT
<213> ORGANISM: Oryza Sativa

<400> SEQUENCE: 1

Lys Gly Ile Ser Gly Thr Phe Thr Asn Val Val Thr Asn Leu Lys Ile
 1               5                  10                  15

<210> SEQ ID NO 2
<211> LENGTH: 13
<212> TYPE: PRT
<213> ORGANISM: Oryza Sativa
```

```
-continued

<400> SEQUENCE: 2

Lys Val Val Leu Val Asp Asn Ala Asp Phe Leu Lys Glu
1               5                   10

<210> SEQ ID NO 3
<211> LENGTH: 37
<212> TYPE: PRT
<213> ORGANISM: Oryza Sativa

<400> SEQUENCE: 3

Lys Ile Val Thr Ser Ala Asn Asn Thr Tyr Glu Ala Gly Val Pro Asn
1               5                   10                  15

Gly Lys Glu Phe Ser Ile Pro Leu Gln Asp Ser Gly His Val Val Gly
            20                  25                  30

Phe Phe Gly Arg Ser
        35

<210> SEQ ID NO 4
<211> LENGTH: 15
<212> TYPE: PRT
<213> ORGANISM: Oryza Sativa

<400> SEQUENCE: 4

Arg Ala Gly Ala Leu Val Asp Ser Ile Gly Val Tyr Val His Ile
1               5                   10                  15

<210> SEQ ID NO 5
<211> LENGTH: 19
<212> TYPE: PRT
<213> ORGANISM: Oryza Sativa

<400> SEQUENCE: 5

Lys Lys Pro Ala Gly Gly Glu Gly Gly Gly Ala His Ile Asn Leu Lys
1               5                   10                  15

Val Lys Gly
```

HIGH THROUGHPUT FUNCTIONAL PROTEOMICS

This application claims priority from U.S. Provisional Application No. 60/305,264, entitled HIGH THROUGHPUT FUNCTIONAL PROTEOMICS, filed Jul. 13, 2001.

FIELD OF THE INVENTION

The present invention relates to an integrated system based on functional affinity chromatography and large scale protein identification. More specifically it is a method of high throughput functional proteomics using a functional affinity column and mass spectrometry. The functional affinity column isolates proteins from a large pool based on a known function as identified by the type of affinity.

BACKGROUND OF THE INVENTION

Most high throughput proteomic methods result in the isolation of a number of proteins for which no function is known. The function is usually deduced using sequence similarities to proteins with known functions or the identification of motifs with a known function. The process can be time-consuming and may not result in the identification of the correct function. Thus, a method is needed which allows for the identification of classes of proteins in a proteome for which a function may be assigned.

SUMMARY OF THE INVENTION

One aspect of the present invention provides a method of identifying proteins with a shared function from a protein pool. The method comprises preparing a protein pool. The protein pool is applied to a functional affinity column wherein the functional affinity column isolates proteins with a common function based on the affinity chromatographic behavior of the proteins. The isolated proteins are analyzed using a one or more dimensional column in combination with mass spectrometry thereby producing spectral information. The isolated proteins are identified by matching the spectral information with a theoretical mass spectrum of a protein having a known sequence.

According to another aspect of the present invention, one or more dimensional chromatography is performed using a high performance liquid chromatography column comprising a strong anion exchange resin followed by a reverse phase resin. In some embodiments, the protein pool can be fractionated prior to application to said functional affinity column. According to some embodiments of the present invention, mass spectrometry is tandem mass spectrometry.

The functional affinity column can comprise a ligand selected from the group consisting of carbohydrate, ATP, phosphate, ECM, metal ion, cell surface peptide, and enzymatic domain. Alternatively, the functional affinity column can comprise a small molecule such as a pharmacophore. In other embodiments the functional affinity column comprises a peptide or protein domain.

Another aspect of the present invention provides a method of ascribing a function to a protein: The method comprises providing a composition containing one or more proteins. The composition is applied to a functional affinity column. Bound proteins are then eluted from the functional affinity column and prepared for mass spectrometry. At least a portion of the eluted protein is analyzed by mass spectrometry thereby producing spectral information. The eluted protein is then identified by matching the spectral information with a theoretical mass spectrum of a protein having a known sequence. The function of the identified protein is ascribed based on the affinity chromatographic behavior of the identified protein.

According to another aspect of the present invention, an eluted protein is subjected to proteolysis and one or more dimensional chromatography. In some embodiments, the one or more dimensional chromatography is performed using a high performance liquid chromatography column comprising a strong anion exchange resin followed by a reverse phase resin.

The protein composition that is applied to the functional affinity column can be a protein extract wherein the protein extract is from a tissue or cell. In some embodiments, the cell is a microbe, a parasite or a cancer cell.

The functional affinity column can comprise a ligand selected from the group consisting of carbohydrate, ATP, phosphate, ECM, metal ion, cell surface peptide, and enzymatic domain. Alternatively, the functional affinity column can comprise a small molecule such as a pharmacophore. In other embodiments the functional affinity column comprises a peptide or protein domain.

In some embodiments of the present invention, the bound protein is eluted from said functional affinity column in a single step. In other embodiments, the bound protein is eluted from said functional affinity column using a stepwise or continuous gradient.

According to one aspect of the present invention, the sequence of the protein having a known sequence is present in a database. According to other aspects, the sequence of the protein having a known sequence is derived from a nucleic acid. In still other aspects, the protein having a known sequence has an unidentified function.

According to yet another aspect of the present invention, an annotated sequence database comprising at least one polypeptide sequence wherein a function of a protein having the at least one polypeptide sequence is ascribed by providing a composition containing one or more proteins. The composition is applied to a functional affinity column. Bound proteins are then eluted from the functional affinity column and prepared for mass spectrometry. At least a portion of the eluted protein is analyzed by mass spectrometry thereby producing spectral information. The eluted protein is then identified by matching the spectral information with a theoretical mass spectrum of a protein having a known sequence. The function of the identified protein is ascribed based on the affinity chromatographic behavior of the identified protein.

According to yet another aspect of the present invention, an annotated sequence database comprising at least one nucleic acid sequence wherein a function of a protein encoded by said at least one nucleic acid sequence is ascribed by providing a composition containing one or more proteins. The composition is applied to a functional affinity column. Bound proteins are then eluted from the functional affinity column and prepared for mass spectrometry. At least a portion of the eluted protein is analyzed by mass spectrometry thereby producing spectral information. The eluted protein is then identified by matching the spectral information with a theoretical mass spectrum of a protein having a known sequence. The function of the identified protein is ascribed based on the affinity chromatographic behavior of the identified protein.

DETAILED DESCRIPTION

Disclosed herein is a method for assigning plausible functions to unknown sequence entries in a particular database. The method involves the isolation of a class of proteins from a cell, tissue, or organism by functional affinity chromatography. The proteins are then further isolated or treated for mass spectrometry (MS). Finally, the proteins are identified using mass spectrometry and numerical comparison of the spectra to theoretical spectra generated from a protein or nucleotide database. Thus, when two or more steps in the process are used, an integrated system which allows for the optimization of proteome analysis results.

In one embodiment, the integrated system includes an appropriately designed affinity column which captures a group of proteins from a given cell that are all related by the fact that they can be ascribed a common function on the basis of their affinity chromatographic behavior. Proteins having similar behavior on a functional affinity column constitute a functional class of proteins. This is then used in combination with analysis via a system based on either Multidimensional Protein Identification Technology (MudPIT) or gel electrophoresis and HPLC in combination with MS/MS in order to identify the proteins which bind to the affinity chromatography column. The resulting data is then used to search for peptide sequences in completely unknown or hypothetical proteins, even in translated raw genomic sequence data, to take a direct short-cut from gene sequence data to plausible function of the encoded protein. Thus, an integrated system based on functional affinity chromatography and large-scale protein identification is provided.

Among other things, the methods described herein may be used to ascribe a function to a protein which has no known function and/or to verify the predicted function of a protein wherein the function of the protein has been deduced by comparing the sequence of the protein with the sequences of homologous proteins having a known function. For example, most high-throughput proteomic methods result in the isolation of a number of proteins for which no function is known. The function is usually deduced using sequence similarities to proteins with known functions or the identification of motifs with a known function. The process can be time-consuming and may not result in the identification of the correct function. However, the present method combines functional affinity chromatography with mass spectrometry to isolate, analyze and identify both known and novel proteins. By careful selection of the affinity ligand, protein function can be assigned as well as protein identity. This method of isolation allows an immediate function to be deduced for the molecule by its ability to bind specific molecules on the affinity column.

In addition, unlike previous methods wherein one or a small class of very specific molecules were to be isolated with the affinity column, the instant method is well suited to the isolation and identification of a broad class of proteins from a tissue.

The approaches described herein also have the advantage that they reduce sample complexity in order to enable the analysis of less abundant cellular components and at the same time provide key functional information along with the identification of the resultant subset of proteins.

In a further embodiment, the subset is then treated for mass spectrometry. There are a variety of chromatographic approaches which may be used for fractionating complex protein mixtures in order to make them more manageable for mass spectrometric analysis. These rely on separation by size, charge, hydrophobicity or other physical properties.

The examples provided herein demonstrate the efficacy of described method for obtaining relevant functional information in addition to protein sequence identification. A great deal of flexibility is available in the specificity of any particular method for isolating target proteins, and the application of such methodology is well suited to the increasing sensitivity of proteomic technology.

Types of Functional Affinity Chromatography

Any type of affinity chromatography can be used in the methods described herein provided that the affinity chromatography isolates proteins which can be grouped together based on function. Typically, affinity chromatography isolates a protein or other molecule based on the type of moiety to which the protein or other molecule binds. The affinity matrix is produced with the binding moiety attached to the matrix. The type of affinity matrix is any matrix which allows the isolation of classes of proteins based on a function. The type of functional affinity matrix can include, but is not limited to, the use of specific parts of proteins, peptides, small molecules or other moieties as ligands, and the function is that of binding to one of these molecules. The type of ligand can be any type which results in the identification of a broad or narrow class of proteins from a protein pool. Using such ligands, a wide variety of functional affinity matrices can be employed in the methods described herein. For example, polysaccharide matrices containing immobilized monosaccharides, polysaccharides or complex carbohydrates can be used to isolate carbohydrate binding proteins. Alternately, extracellular matrix (ECM) binding proteins can be isolated using an ECM binding region, such as Arginine-Glycine-Aspartate (RGD). Other examples include metal ions (for metalloproteases), phosphate (or analog) ions (for phosphatases/kinases), ATP (for ATP binding proteins), cell surface peptide domains from specific cell types, small molecules or drugs, adhesion domains, and cellular recognition domains (for example, those from proteins including fibronectin, veg-F, and NCAM). Because of the method of isolation, an immediate function is deduced for a molecule isolated by this technique by its ability to bind the specific moiety or molecule which is part of the affinity column.

Functional affinity chromatography may be thought of as an activity-based protein fractionation which reduces sample complexity, while at the same time, assigning a known function to those proteins that are isolated. Thus, in one embodiment, the function may be broad-based, for example the use of polysaccharide matrices to isolate carbohydrate binding proteins. Whole functionally related families (or classes) of proteins may be isolated through the use of an appropriate functional affinity matrix, for example the isolation of calcium-binding proteins with calmodulin. In a further embodiment, the function may be more specific than simply the binding to a protein, for example a receptor. Rather, in this case, a specific domain or activity region of the receptor may be identified and used to produce a functional affinity chromatography column. Any proteins which bind would have a definite function based on which domain were used for the functional affinity column.

In accordance with one embodiment of the methods described herein, the functional affinity chromatography may be carried out using carbohydrate binding matrices or sugar-agarose resins, including but not limited to, galactose, glucose, mannose, fucose, n-acetyl glucosamine, n-acetyl galactosamine, lactose or melibiose coupled to agarose. Alternatively, specific resins which have other types of carbohydrate moieties can be produced using methods known in the art. The carbohydrates and resins may be purchased from a number of vendors. For example the carbohydrates may be purchased from E-Y laboratories (San Mateo, Calif.) D-mannose, (catalog #C-6009-25), N-acetyl-D-galactosamine, (catalog #C-6000-1), N-acetyl-D-glucosamine, (catalog #C-6001-100), and alpha-L-fucose, (catalog #G-6002-5). The resins may be purchased from E-Y laboratories (San Mateo, Calif.) D-mannose gel, (catalog #CG-005-5), N-acetyl-galactosamine gel, (catalog #CG-002-5), N-acetyl-glucosamine gel, (catalog #CG-003-5), and alpha-L-fucose gel, (catalog #CG-001-5).

In a further embodiment, the functional affinity chromatography may be a protein or peptide affinity chromatography, in which the protein or peptide is chosen to define a function for the molecules which bind. For example, a ligand binding domain of a receptor may be chosen and the resulting proteins may be defined as alternative ligands for that specific receptor. Alternatively, a variety of extracellular peptide domains may be chosen from a specific cell type (for example, an intracellular parasite or pathogenic microbe) and the resulting proteins may be defined as being involved in the extracellular interaction and signaling for that cell type.

In a further embodiment, a functional affinity chromatography ligand may be a small molecule which, for example, is selected on the basis of activity in a cell based phenotypic assay. A functional affinity column possessing such a small molecule ligand can lead to the identification of those proteins whose function is to interact with the small molecule (or molecules) in a cell. Alternatively, the small molecules can be a pharmacophore. A pharmacophore is the active structural portion of a pharmaceutical compound. In other words, a pharmacophore is the minimum functionality a molecule has to contain in order to exhibit activity. Only molecules which interact with the same protein in the same way will share a pharmacophore. As such, if an isolated or synthesized pharmacophore is implemented as a functional affinity chromatography ligand, isolation of proteins that bind to the pharmacophore will lead to the identification of protein(s) that function in the specific pharmaceutical interaction. For example, proteins that function as targets for pharmaceuticals, such as antineoplastic agents, anesthetics, antihypertensive agents, anti-depressants, anti-convulsants, antihistamines, antibacterial agents, antifungal agents, antiparasitic agents, hormone antagonists, immunomodulators, neurotransmitter antagonists, and antiglaucoma agents, can be identified.

In one embodiment, a functional affinity chromatography does not include isolation of glycoproteins or phosphoproteins as such isolation does not define a function for the protein, but only the type of protein. For example, an affinity column wherein the ligand is a lectin provides for the isolation of glycosylated proteins but does not necessarily provide any information about the function of the isolated proteins.

Increasing specificity may be obtained by appropriate selection of the affinity ligand. In one embodiment, a chemical probe can be used to screen for proteins having a desired specificity. Studies of this kind have largely been limited to the isolation of one specific protein based on a known activity. However, the method herein can be used to isolate families of proteins based on their specific reactivity to the chemical probe.

A further embodiment uses a mixed affinity column as a functional affinity column which can be produced to isolate a variety of molecules capable of binding to a cell, virus, or a specific tissue (see Example 6). In this case, the affinity ligand which is part of the matrix may be specific portions of receptors (e.g., peptides or protein domains). In one embodiment, the extracellular portion of the receptor is used, more particularly the extracellular binding domain. The receptor proteins which will be used to produce the affinity column can be isolated in any way known to one of skill in the art. For example, whole living cultured cells of a given genus and species (e.g. *Plasmodium falciparum*, the causative agent of malaria, and *Neiserria gonorrhoeae*, the causative agent of gonorrhea) can be subjected to trypsinization or alternative types of proteolysis. The peptides released from surface proteins of the organism can then be attached to an affinity column and any proteins which bind to that affinity column may be used to learn more about host/parasite or host/pathogen interactions. Alternatively, a mixture of a certain type of cancer cell may be subjected to trypsinization and the proteins which are cleaved may be attached to a matrix to produce an affinity column and in this way more can be learned about the interaction between a normal human cell and a cancer cell.

In some embodiments the entire receptor protein of the host cell is used as the functional affinity ligand. In other embodiments, only certain portions of the receptor are used.

In a further embodiment, the methods described herein can be used to identify extracellular matrix (ECM) binding molecules using a binding site which is typically found on ECM proteins as the affinity ligand bound to the matrix.

In one embodiment, the method may also be used to analyze changes in the lectin complement profile in natural or engineered mutant plant or animal strains, in treated or untreated samples, or in specific disease states. Additionally, some of these novel proteins can be further purified and developed on the basis of their in vivo physiological function. For example, a novel *Oryza saliva* mannose isomerase might be overexpressed in plant cell lines as a means of more closely matching the native glycosylation of stably or transiently transfected recombinant human glycoproteins, thus providing a high yield, low cost source of such proteins. Such functional protein identification and subsequent engineering be of particular importance in the production of human-like antibodies in plants.

In one embodiment, the functional affinity chromatography ligand is selected from the group consisting of carbohydrate, metal, small molecule, peptide, and protein domain. In a further embodiment, the functional affinity chromatography ligand is small molecule. In a further embodiment, the functional affinity chromatography ligand is peptide and/or protein domain. In a further embodiment, the functional affinity chromatography ligand is carbohydrate.

Tissue Types

It is envisioned that any homogeneous cell or tissue type can be analyzed using the method. Examples are red blood cells, liver cells, parasites, microbes from a given species, cancer cells, cells from a specific plant tissue such as leaves, cells which have been treated with a specific chemical or pharmaceutical, cells of varying developmental stages and other cells of interest. Additionally, viruses and other protein particles may be analyzed.

In a further embodiment, the cell is chosen based on the time during the cell cycle, development, immune activation, after treatment with a mitogen, during development, during a disease state, during treatment. In fact, the proteome may be analyzed from a treated cell compared to an untreated cell. This may provide information about the effect of a treatment or cellular state on the proteome of that cell.

It is envisioned that the choice of cell or tissue may have a large effect on the function which is deduced. For example, if a Plasmodium extracellular peptide domain functional affinity chromatography column is used, and a sample from human red blood cells is applied, then the human proteins involved in the host parasite interaction can be identified.

Sample Treatment

An extract of the proteins found in a cell or tissue is prepared, removing any components which may interfere with chromatography. The extract is then applied to the affinity column. Alternatively, the extract is treated with a protease and then applied to the affinity column. However, it will be appreciated by one of skill in the art that treating proteins with a protease may affect the ability of the protein to bind to its natural ligand. Additionally, it will be appreciated that the sample can be processed prior to application to the affinity column. Processing of a protein extract or other composition containing the one or more proteins of interest can be performed using methods well known in the art, including but not limited to, chromatography, protein precipitation, and centrifugation. For example, the proteins of a specific functional class which are located only in plant cell chloroplasts can be obtained by first fractionating the contents of the plant cell of interest by centrifugation in order to obtain a purified or substantially enriched preparation of chloroplasts. The proteins from the chloroplast fraction can then be applied to the function affinity column. One of ordinary skill in the art will recognize that a wide variety of pre-affinity column fractionations of cellular proteins may be used prior to the affinity chromatography step.

After the binding of the proteins of interest to the functional affinity column, the column can be washed to remove all non-binding proteins. The bound proteins are then eluted from the affinity column and further processed for mass spectrometry.

Further Processing of Proteins of Interest For MS Analysis

After elution, the eluted proteins are further separated and/or treated for mass spectrometry. This preparation for mass spectrometry can be accomplished in a number of ways. The samples may be separated by one-dimensional or two-dimensional electrophoresis. In one-dimensional electrophoresis, gels are run according to methods well known in the art, such as the use of a BioRad mini gel system with pre cast acrylamide gels. In the two-dimensional electrophoresis, eluted proteins are diluted into a sample solubilization buffer comprised of 7M urea, 2M thiourea, 30 mM DTT, and 0.5% Triton X-100. The first dimension for isoelectric focusing is carried out on a BioRad IPG system essentially as described by the manufacturer. Immobilized pH gradient strips are run for 30–45K volt hours. Prior to loading the IEF strips on the second dimension, the strips are re-equilibrated with a solution (2% SDS, 50 mM Tris, pH 6.9, 10% glycerol, and 7 mM urea) and directly applied to a BioRad 8–16% gradient SDS-PAGE gel for electrophoresis. The resultant gels are stained with silver or Sypro ruby, according to methods well established in the art. Protein spots are cut from the gel either manually or by using a robotic gel excision system. Gel pieces are then put onto a Micromass digest robot for trypsin digest and peptide extraction, and the extracts analyzed by tandem mass spectrometry (MS/MS).

It will be appreciated that two-dimensional preparative electrophoresis is not limited to isoelectric focusing followed by gradient gel electrophoresis. For example, other two-dimensional gel approaches can also be employed, such as blue native electrophoresis followed by PAGE or non-reducing PAGE followed by reducing SDS-PAGE.

In an alternative embodiment, preparative treatment of eluted proteins prior to mass spectrometry analysis relies on further chromatographic separation of peptide fragments generated by proteolysis of the eluted proteins. The resultant peptide mixture can be subjected to one- or multi-dimensional chromatography column prior to mass spectrometry analysis. A high throughput adaptation of such treatment is the application of the protein mixture to multidimensional protein identification technology (MudPIT) (see U.S. Provisional Application No. 60/305,231, filed Jul. 13, 2001, the disclosure of which is incorporated herein by reference in its entirety). See also Washburn, et al. Nature Biotechnology 19:March 2001;pp. 242–247. Typically, the protein mixture is treated with a protease prior to MudPIT. The mixture is then run over a mixed matrix comprising a strong cation exchange matrix stacked with a reverse-phase matrix. The matrices are stacked such that as proteins are eluted from one matrix they bind to the second. Finally, as the proteins are eluted from the MudPIT column they are immediately subject to tandem MS and identified by comparing the resultant mass spectra to theoretical mass spectra generated from protein or DNA databases by the SEQUEST algorithm (See Yates, III, et al., U.S. Pat. No. 5,538,897, issued Jul. 23, 1996, the disclosure of which is incorporated herein by reference in its entirety).

In certain embodiments, a two-dimensional HPLC column comprising a strong anion exchange resin stacked adjacent to a reverse-phase resin is contemplated. The peptide mixture is first subjected to the anion exchanger then subsequently to the hydrophobic interaction resin.

MS Analysis

In some embodiments, when using the MudPIT technology for further processing of the protein sample, the MudPIT column is attached in tandem to the MS and the samples are immediately analyzed. It will be appreciated, however, that additional treatment of the protein or peptide mixture may allow for further analysis using MS. One of skill in the art will also recognize that the sample applied to MS should be in an MS compatible buffer and be of a quality that can be analyzed by MS.

Mass spectrometry is a very useful technique for measuring the molecular weights of proteins and polypeptides. The term "mass spectrometry" is used herein in its usual sense to include various methods such as tandem mass spectrometry, matrix assisted laser desorption ionization (MALDI) time-of-flight (TOF) mass spectrometers (MS), MALDI-TOF-TOF MS, MALDI Quadrupole-time-of-flight (Q-TOF) MS, electrospray ionization (ESI)-TOF MS, ESI-Q-TOF, ESI-TOF-TOF, ESI-ion trap MS, ESI Triple quadrupole MS, ESI Fourier Transform Mass Spectrometry (FTMS), MALDI-FTMS, MALDI-Ion Trap-TOF, and ESI-Ion Trap TOF.

These mass spectrometry methods are well known in the art, see e.g., Chapters 1–4 etc. of Gary Siuzdak, "Mass Spectrometry for Biotechnology," Academic Press, N.Y., (1996). At its most basic level, mass spectrometry involves ionizing a molecule and then measuring the mass of the resulting ion. Since molecules ionize in a way that is well known, the molecular weight of the molecule can generally be accurately determined from the mass of the ion.

Using genomic sequence information, it is theoretically possible to predict the entire set of proteins possibly expressed by a particular organism by translating all possible open reading frames, and to use this information to predict the molecular weights of all the possible proteins. By putting this information into a computerized protein database, it is therefore theoretically possible to identify all the proteins in an organism by determining the molecular weights of the proteins by mass spectrometry and comparing the molecular weights obtained to the molecular weights of the proteins in the database. However, in practice such an undertaking is extremely difficult for complicated mixtures of proteins because different proteins may have the same molecular weight and/or because many mass spectrometry techniques do not have the requisite resolution to distinguish proteins having very similar molecular weights.

Tandem mass spectrometry has been used to identify proteins because it can provide information in addition to parent ion molecular weight. Tandem mass spectrometry involves first obtaining a mass spectrum of the ion of interest, then fragmenting that ion and obtaining a mass spectrum of the fragments. Tandem mass spectrometry thus provides both molecular weight information and a fragmentation pattern that can be used in combination along with the molecular weight information to identify the protein. Tandem mass spectrometry, however, tends to be slower than techniques that provide only molecular weight information because fragmentation and analysis of the fragments takes additional time.

One embodiment of the methods described herein provides a high throughput process for the identification of functional classes of proteins from a tissue or cell comprising providing a composition containing one or more proteins of interest, such as a crude extract containing proteins from a tissue or cell type, applying the composition to a functional affinity column, eluting the proteins which bind to the column, preparing the eluted proteins for further analysis by mass spectrometry, such as subjecting the eluted proteins to proteolysis to one- or multi-dimensional chromatography (e.g. MudPIT), analyzing at least a portion (e.g. a peptide fragment) of an eluted protein of interest by mass spectrometry to obtain spectral information, and identifying the eluted protein by matching the spectral information with a theoretical mass spectrum of a protein having a known sequence. As used herein, the phrase, "at least a portion of an eluted protein" can include one or more peptide fragments obtained from the eluted protein. Alternatively, this phrase may refer to the entire eluted protein.

In other embodiments of the methods described herein, a function can be ascribed to any of the proteins identified by mass spectrometry analysis. The polypeptide sequences of proteins that are isolated by functional affinity may be known and/or present in a sequence database. In some cases, the polypeptide sequence of the isolated protein may have been previously derived from a nucleic acid sequence obtained from genome sequencing or other sequencing efforts. In such cases, the predicted protein may be a putative protein or a protein with no known function. In other cases, the protein may have a predicted function that was derived from comparison of the polypeptide sequence of the protein with the sequences of homologous proteins having a known function. Alternatively, the protein isolated from the functional affinity column may have a novel polypeptide sequence.

In any of the above cases, the methods described herein can be used to ascribe a function to such proteins. For example, if the protein isolated from the functional affinity column has a known polypeptide sequence, the, spectral information can be used to match the isolated protein with its corresponding polypeptide sequence in the database. The functional information obtained from the functional affinity chromatography can then be used to verify the predicted function of the database sequence or to ascribe a function to a database sequence having no predicted function.

In an alternative embodiment, the sequence that is isolated by functional affinity chromatography is previously unknown. Although desirable, it is not necessary to obtain a complete polypeptide sequence in order to establish the identity of a novel protein. Partial sequence information combine with other physical information such as the molecular weight and isoelectric point (pI) of the protein is sufficient to identify a novel protein especially when such information is combine with the functional information obtained from the functional affinity chromatography step.

In some cases, the sequence information that is produced by tandem mass spectrometry can lead to the establishment of a full-length polypeptide sequence. Accordingly, this full-length sequence information can be combine with the functional information produced by functional affinity chromatography to ascribe a function to the newly identified protein. It will be appreciated that a several techniques can be used to obtain a complete sequence from peptide sequence data. In some cases, sequencing of the each peptide of the entire protein may be possible. Alternatively, methods using peptide sequence data for obtaining a nucleic acid which encodes the full-length protein are well known in the art.

A further embodiment is a method for the identification of functional classes of proteins from a tissue or cell comprising isolating a crude extract containing proteins from a tissue or cell type. In certain embodiments, the isolation of a crude extract can be achieved by releasing surface peptides from whole cells. The crude extract is then applied to a functional affinity column and the proteins which bind to the column are eluted. The eluted proteins can be prepared for analysis by mass spectrometry. The preparation of the eluted proteins for mass spectrometry generally comprises proteolysis of the eluted protein and separation of the peptide fragments by HPLC using one- or multi-dimensional chromatography. Additional preparation steps, such as electrophoresis, can be added or used to replace certain preparation procedures. At least a portion, such as one or more peptide fragments, of a prepared, eluted protein of interest is then analyzed by mass spectrometry to obtain spectral information. The spectral information is used to identify the eluted protein by matching the spectral information with a theoretical mass spectrum of a protein having a known sequence. Alternatively, the spectral information can be used to directly establish the identity of the protein.

In some embodiments of the methods described herein, the functional affinity chromatography ligand that is used is carbohydrate or ECM affinity chromatography. In other embodiments, the functional affinity chromatography ligand is selected from the group consisting of carbohydrate, metal, small molecule, peptide, and protein domain.

The carbohydrate affinity ligand can include, but is not limited to, glucose, mannose, galactose, xylose, arabinose, N-Acetyl-D-glucosamine, N-Acetyl-D-galactosamine, sialic acid, fucose, lactose, and melobiose. Additionally, the functional affinity column may be a mixed bed carbohydrate column and the peptides may be eluted sequentially.

The methods described herein will be described in more detail below with reference to a specific example the use of various sugar affinity matrices to isolate carbohydrate binding proteins (lectins). Recognition between proteins and carbohydrates is important in a variety of processes; lectins are involved in N and O-glycan biosynthesis and maturation, tagging and recognition of proteins for proteolytic degradation, folding, cell-cell interaction or cell adhesion, and transport to a specific secretory pathway. They are used extensively in the isolation and characterization of glycoproteins. They are also used to precipitate polysaccharides and glycoproteins from solution, for tagging, visualizing, and isolating membrane glycolipids, and for mitogenic stimulation of mammalian T or B lymphocytes. Many currently available lectins were originally identified in plant tissues.

Affinity chromatography in combination with mass spectrometry was used herein to isolate, analyze and identify carbohydrate binding proteins from rice. Affinity purification of rice tissue extracts through binding to carbohydrate resins allowed the identification and isolation of lectins.

Having now generally described the invention, the following examples are offered to illustrate, but not to limit the claimed invention.

EXAMPLES

Examples 1–4 set out a use of the method of the invention to isolate rice lectins. In brief, samples of the soluble fraction of crude rice leaf and rice root extracts were applied to an affinity chromatography column. The affinity chromatography column comprised carbohydrate residues linked to agarose. The bound proteins were eluted and analyzed using the following procedures: First, eluted proteins were run on an SDS polyacrylamide gel. Next, the gels were silver stained and image analysis was used to identify proteins of interest. The protein bands of interest were cut from the gels and trypsinized. The trypsinized peptides were analyzed by mass spectrometry and identified by searching the data against protein databases.

Example 1 provides the method for producing the protein extracts.

Example 1
Preparation of Soluble Rice Protein Extracts

Thirty to fifty grams of leaves or roots from *Oryza sativa* (6 flats of 6-week old plants) were snap frozen in liquid nitrogen, and the tissue ground into ice-cold extraction buffer (10 mM Tris, pH 7.2, 150 mM NaCl, 0.5% Triton X-100, 1% sodium deoxycholate, protease inhibitors). Tissue was allowed to solubilize, for 5 minutes with stirring, on ice. Crude tissue extract was filtered through cheesecloth (2X), and then miracloth (1X) to remove particulate matter. Insoluble material was spun out at 10,000 g, for 15 minutes at 4° C. The supernatant was then filtered sterilized through a 0.2 micron Nalgene filter, concentrated to at least 10 mg/ml on an Amicon stirred cell using a YM3 molecular weight cut-off membrane, and dialyzed overnight into column equilibration buffer. Aliquots were stored at −80° C.

In Example 2 functional affinity chromatography is performed.

Figure 1:
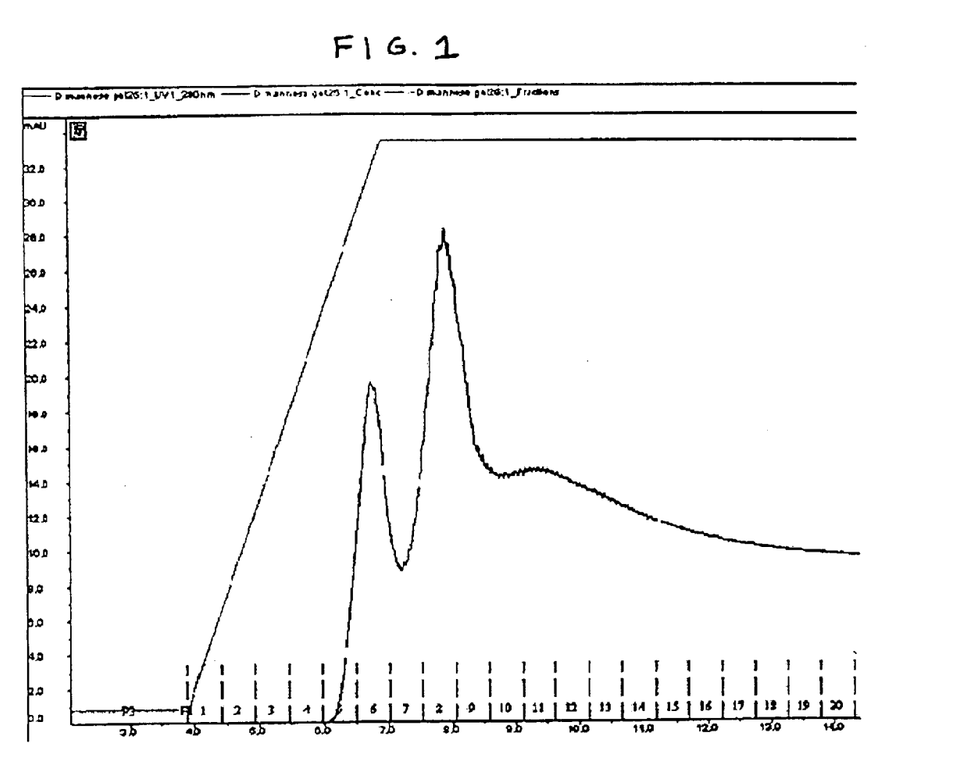
FIG. 1 is an elution profile of soluble rice leaf extract chromatographed over a mannose-agarose affinity column linked to a Pharmacia AKTA FPLC system.

Example 2
Isolation of Carbohydrate Binding Proteins by Functional Affinity Chromatography Columns consisting of either D-mannose, N-Acetyl-D-glucosamine (GlcNAc), N-acetyl-galactosamine (GalNAc) or α-L-fucose carbohydrate residues bound to agarose beads were equilibrated in the appropriate buffer (50 mM Tris, pH 7.5, 150 mM NaCl, 2 mM $CaCl_2$, 2 mM $MgCl_2$ for mannose, fucose, and GlcNAc columns, or 20 mM Bis-Tris, pH 7.0, 50 mM NaCl, 0.1% reduced Triton-X 100, 2 mM $CaCl_2$, 2 MM $MgCl_2$, for the GalNAc column) over 5 column volumes. The columns were purchased from E-Y laboratories (San Mateo, Calif.) D-mannose gel, catalog #CG-005-5, N-acetyl-galactosamine gel, catalog #CG-002-5, N-acetyl-glucosamine gel, catalog #CG-003-5, and alpha-L-fucose gel, catalog #CG-001-5. The protein extract of interest was loaded onto the column at a rate of 0.2 ml/minute, and allowed to bind for 30 minutes at 4° C. Bound proteins were then eluted over a continuous gradient of 10 column volumes from 0–100% buffer B (equilibration buffer and 500 mM of the column specific carbohydrate). FIG. 1 shows the elution profile of soluble rice leaf extract that was chromatographed over a mannose-agarose column. Eluate was collected in 500 μl fractions. The UV absorbance peaks show fractions containing proteins of interest which bound to the mannose affinity matrix (see FIG. 1, fractions 6, 8 and 9).

In Example 3 the proteins are subjected to MS.

Figure 2:
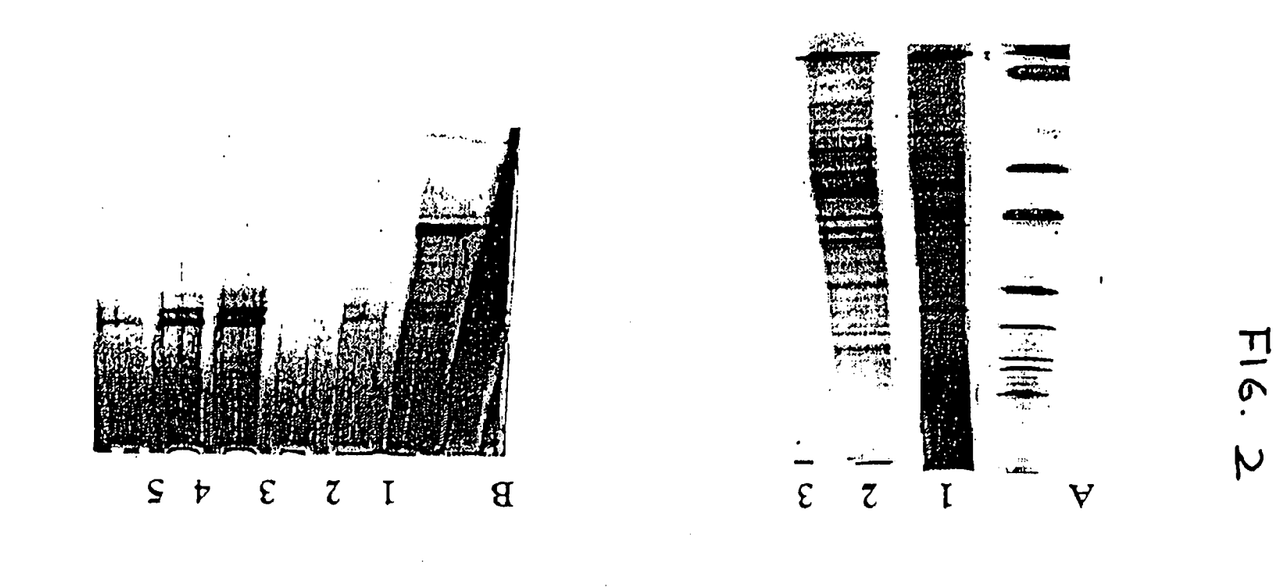
FIG. 2A depicts an SDS polyacrylamide gel showing the whole protein extract (lane 1) and the entire protein fraction that binds to the mannose-agarose affinity column (lane 2).
FIG. 2B depicts an SDS polyacrylamide gel showing proteins present in peak protein fractions isolated from soluble leaf extract after chromatography over a mannose-agarose affinity column (lanes 1 to 5).

Example 3
Preparation of Samples and Identification and Analysis of Proteins Using Mass Spectrometry Analysis Peak fractions were analyzed by SDS-PAGE under reducing conditions. FIG. 2A shows proteins from the whole protein extract (lane 1) and the entire protein fraction that binds to the mannose-agarose affinity column (lane 2). FIG. 2B shows proteins present in peak protein fractions isolated from soluble leaf extract after chromatography over a mannose-agarose affinity column (lanes 1 to 5 correspond to fractions 6 to 10 in FIG. 1). Silver-stained protein bands were excised, and the proteins extracted and trypsin digested by incubation overnight at 37° C., then buffer exchanged into 0.1% formic acid preparatory to mass spectrometric analysis by liquid chromatography and tandem MS (LC-MS/MS) using a Finnigan LCQ ion trap mass spectrometer as follows:

For one-dimensional electrophoresis, gels were run according to established methods using a BioRad mini-gel system and BioRad pre-cast gels. Protein bands from one-dimensional gels were visualized with silver staining, excised manually, and transferred to 96-well plates. The plates were transferred to a Massprep digestion robot (Micromass, Beverley, Mass.) for destaining and in-gel digestion with trypsin. Following digestion, tryptic peptides were extracted from the gel pieces with 5% formic acid/ 5% $CH_3CN$ on the Massprep robot. The extracted peptides were diluted to 100 μl per well with 0.1% formic acid.

A microbore HPLC system (Surveyor, ThermoFinnigan, San Jose, Calif.) was modified to operate at capillary flow rates using a simple T-piece flow-splitter. Columns (10 cm×75 μm I.D.) were prepared by packing 100 Å, 5 μm Zorbax C18 resin at 500 psi pressure into New Objectives Pico Frits (New Objectives, MA) columns with integral spray needles. Peptides were eluted in a gradient using buffer A (5% v/v acetonitrile, 0.1% formic acid) and buffer B (90% v/v acetonitrile, 0.1% formic acid), at a flow rate of 300 n/min. Following an initial wash with buffer A for 10 minutes, peptides were eluted with a linear gradient from 0–100% buffer B over a 30 minute interval. Samples were introduced onto the analytical column using a Surveyor autosampler (Surveyor, ThermoFinnigan, San Jose, Calif.) which first transferred the 100 µl peptide extract onto a C18 (300 µm×5 mm) cartridge (LC Packings, San Francisco, Calif.) and then used a switching valve to transfer the eluted peptides on to the analytical column. The HPLC column eluant was eluted directly into the electrospray ionization source of a ThermoFinnigan LCQ-Deca ion trap mass spectrometer (ThermoFinnigan, San Jose, Calif.). Spectra were scanned over the range 400–1400 mass units. Automated peak recognition, dynamic exclusion, and daughter ion scanning of the top two most intense ions were performed using the Xcalibur software according to published methods (Washburn, et al. *Nature Biotechnol.* 19;242-47), as described previously.

MS/MS data were analyzed using SEQUEST (Finnigan, Corp.), a computer program that allows the correlation of experimental data with theoretical spectra generated from known protein sequences. In this work, the criteria for a preliminary positive peptide identification for a doubly-charged peptide were a correlation factor (Xcorr) greater than 2.5, a delta cross-correlation factor (δXcorr) greater than 0.1 (indicating a significant difference between the best match reported and the next best match), a minimum of one tryptic peptide terminus, and a high preliminary scoring. For triply-charged peptides the correlation factor threshold was set at 3.5. All matched peptides were confirmed by visual examination of the spectra. All spectra were searched against a composite database containing the latest version of a proprietary rice genomic database, and a combined cereals database assembled from the public non-redundant protein database (SwissProt). In cases where peptides were identified from unannotated sequence data, identifications were further annotated where possible by BLAST homology searching.

Figure 3:
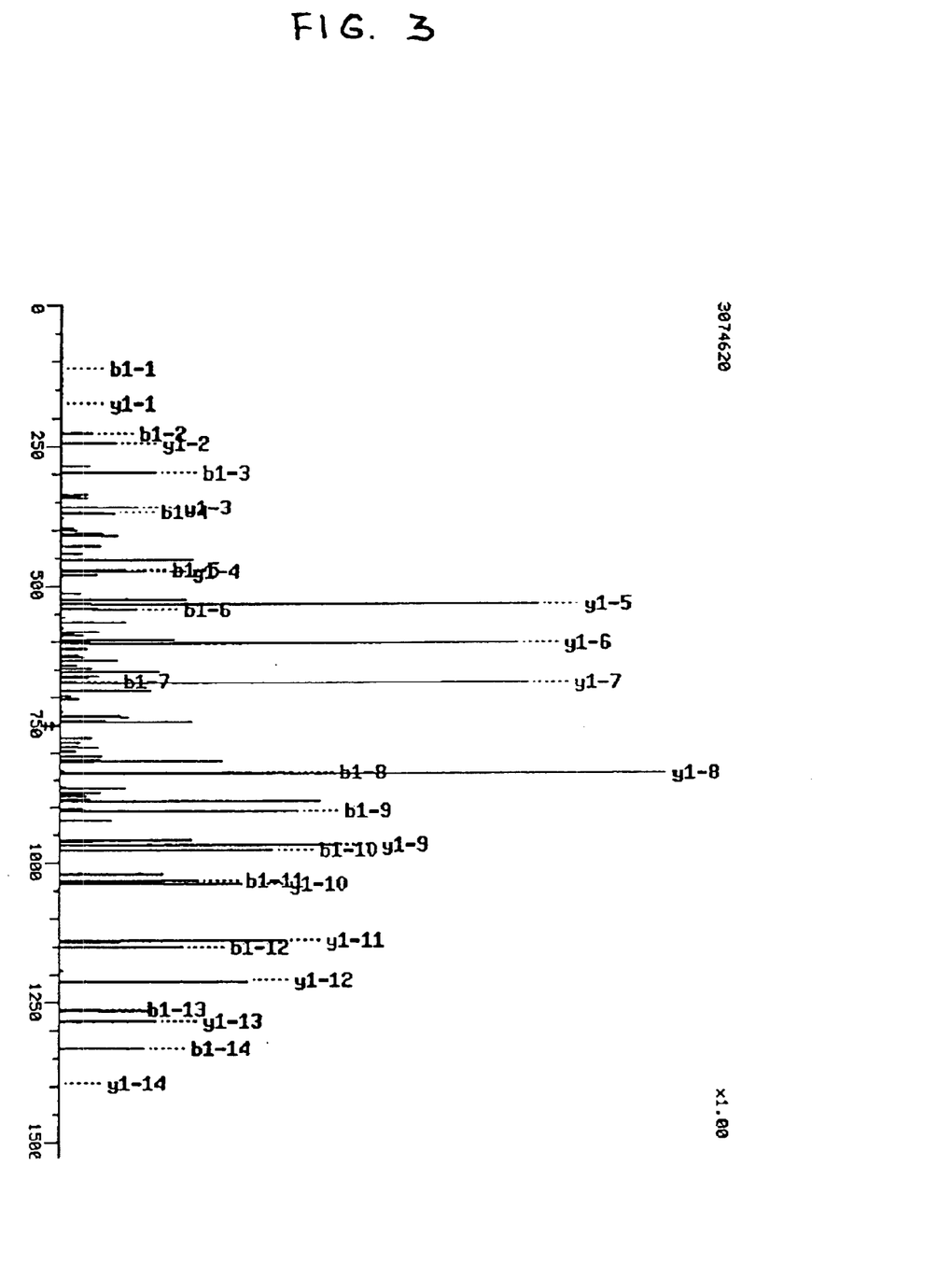
FIG. 3 is a tandem mass spectrum of a single peptide from a mixture of rice leaf extract proteins that bound to a GlcNAc-agarose resin. The spectrum was used to identify the isolated tryptic peptide thereby permitting the identification of the corresponding protein.

All analyses were performed on a Finnigan LCQ ion trap mass spectrometer. The peptide sequence raw data was searched against a database by SEQUEST software. A number of criteria were considered in assigning peptide and protein identifications: the statistical score from SEQUEST, Xcorr, δXcorr, the peptide length and terminal sequence, the quality of the spectrum from the peptides, the number of peptides from the same protein band that were identified in the same search, and the molecular weight and pI of the protein. FIG. 3 shows an example of spectral information obtained from a tryptic peptide corresponding to a protein isolated from a GlcNAc affinity column.

Example 4 provides the results of the affinity chromatography and MS analysis.

Example 4
Protein Identification and Source

The following data includes some examples of the proteins which were identified. Some proteins were identified in more than one tissue, or from binding more than one tissue, or from binding more than one carbohydrate resin. The data is presented in very abbreviated form, and is divided into three categories, each of which demonstrates a distinct feature of the method. First, the isolation of known carbohydrate binding proteins as proof of concept. Second, the detection of little or no non-specific binding. Third, the identification of proteins not previously known to be carbohydrate binding proteins.

The data in Table 1 includes a comparison of mass spectrum data for experimentally isolated proteins with the theoretical mass spectra for proteins having a known sequence from *Oryza saliva* (rice). Each of the experimentally isolated proteins in Table 1 corresponds to a sequence that has been identified in rice and has been assigned a function. Table 1 specifically includes the Xcorr score for the mass spectral comparisons. If the first number listed (Xcorr) is greater than 2.5 and the second number (δXcorr) is greater than 0.1, the score suggests close identity. Additional information regarding the statistical comparisons of mass spectrometry data can be found in Washburn et al. Nature Biotechnology Volume 19, March 2001, Pages 242–247 and Haynes et al. Electrophoresis, May 1998, volume 19, No. 6, Pages 939–065, the disclosures of which are incorporated herein by reference in their entireties.

TABLE 1

Results and Analysis of Mass Spectra Comparisons

| Sample ID | Xcorr | Delta Xcorr | Pep. mass | Peptide sequence | Protein Database entry | Protein header information |
|---|---|---|---|---|---|---|
| Leaf/mannose: Band 10 | 3.725 | 0.261 | 1337.2 | K.GISGTFTN VVTNLK.I (SEQ ID NO: 1) | SW:GOS9_ORYSA | P27349 *oryza sativa* (rice). gos9 protein. 8/1992 [MASS = 14120] Lectin 3, putative Mannose-binding protein. Jacalin homolog. |
| Leaf/mannose: Band 5 | 2.491 | 0.120 | 903.9 | K.VVLVDNA DFLK.E (SEQ ID NO: 2) | GP:AB017042_1 | *Oryza sativa* mRNA for glyoxalase I, complete eds; putative. [MASS = 32553] |
| Leaf/GlcNAc: whole fraction | 3.535 | 0.254 | 626.5 | K.IVTSANNT YEAGVPNG KEFSIPLQDS GHVVGFFGR .S (SEQ ID NO: 3) | SW:SALT_ORYSA | ORYSA P24120 *oryza sativa* (rice). salt-stress induced protein (salt protein). 7/1998 [MASS = 15066] Mannose-binding Jacalin related lectin. |
| Leaf/GlcNAc: whole fraction | 2.168 | 0.301 | 1232.9 | R.AGALVDSI GVYVHI (SEQ ID NO: 4) | SW:GOS9_ORYSA | P27349 *Oryza sativa* (rice). gos9 protein. 8/1992 [MASS = 14120] Lectin 3, putative Mannose-binding protein. Jacalin homolog. |

TABLE 1-continued

Results and Analysis of Mass Spectra Comparisons

| Sample ID | Xcorr | Delta Xcorr | Pep. mass | Peptide sequence | Protein Database entry | Protein header information |
|---|---|---|---|---|---|---|
| Leaf/GlcNAc: whole fraction | 2.353 | 0.063 | 385.8 | K.KPAGGEG GGAHINLKV K.G (SEQ ID NO: 5) | GP:OSA5841_1 | *Oryza sativa* (rice). ubiquitin like protein smt3 7/1998 [MASS = 10928] |

The data presented in Table 1 shows that functional affinity chromatography followed by mass spectrometry is an effective means for isolating and identifying specific functional classes of proteins. In particular, the following data from Table 1 specifically demonstrates the isolation and identification of proteins that bind to either the mannose or GlcNAc functional affinity matrices.

Leaf/mannose: Band 10: GOS9 SW:GOS9_ORYSA

Leaf/mannose: Band 5: glyoxylase 1 GP:AB017042

Leaf/GlcNAc: whole fraction: salt stress induced protein SW:SALT_ORYSA

Leaf/GlcNAc: whole fraction: ubiquitin like protein SMT-3 SW:SMT3_ORYSA

Additionally, the data presented in Table 1 shows that when functional affinity chromatography followed by mass spectrometry is used as a means for isolating and identifying specific functional classes of proteins, insubstantial non-specific binding is detected. Specifically, of the 30 samples analyzed, no highly expressed but non-specific proteins, such as ribulose 1,5-bisphosphate carboxylase or glutelin was detected in any sample.

In addition to the above results, lectins from rice were obtained did not have a matching polypeptide sequence from rice available in the publicly available sequence databases. However, many of these proteins matched annotated sequences from other organisms. Although some of the polypeptides from other organisms were predicted to bind carbohydrates, the remainder of these polypeptides had no known function. Accordingly, the functional affinity chromatography/mass spectrometry method described herein could be used to ascribe a function to each of these proteins. Such results are presented in Table 2.

TABLE 2

Isolated Proteins Without Matches to Publicly Available Rice Sequences

| Sample ID | Protein Database entry | Organism | Annotation |
|---|---|---|---|
| Leaf/mannose: Band 1 | SW:UDPG_HORVU | Barely | Rutp glucose-1-phosphate uridylyl-transferase |
| Leaf/mannose: Band 2 | AC012563.3_27 | *Arabidopsis thaliana* | hydroxy-pyruvate reductase |
| Leaf/mannose: Band 2 | AC007209.5_3 | *Arabidopsis thaliana* | alanine glyoxylate amino-transferase |
| Leaf/mannose: Band 10 | AC021640.5_39 | *Arabidopsis thaliana* | putative mannose-6-phosphate isomerase |

TABLE 2-continued

Isolated Proteins Without Matches to Publicly Available Rice Sequences

| Sample ID | Protein Database entry | Organism | Annotation |
|---|---|---|---|
| Leaf/mannose: Band 11 | X92975.1_0 | *Arabidopsis thaliana* | xyloglucan endo trans-glycosylase |
| Leaf/GlcNAc: whole fraction | AC005679.1_6 | *Arabidopsis thaliana* | Putative protein |
| Root/Mannose: whole fraction | OS012136 | *Arabidopsis thaliana* | Similar to protein kinase |
| Root/Mannose: whole fraction | AL163792.1_9 | *Arabidopsis thaliana* | Similarity to DRH1 DEAD box protein |

Some of the proteins that were isolated from rice matched polypeptide sequences from a proprietary rice database that had no previously known function. Such data is provided in Table 3.

TABLE 3

Isolated Proteins Matching Proprietary Rice Sequences of Unknown Function

| Sample ID | Protein Database entry | Organism | Annotation |
|---|---|---|---|
| Leaf/mannose: Band 2 | OS009419 | *Oryza sativa* | Similarity to zinc finger protein |
| Leaf/mannose: Band 5 | OS005858 | *Oryza sativa* | similarity to peroxidase |
| Leaf/mannose: Band 8 | OS005470 | *Oryza sativa* | putative ribose-5-phosphate isomerase |
| Leaf/mannose: Band 9 | CLO28657.7 | *Oryza sativa* | hypothetical protein |
| Leaf/GlcNAc: whole fraction | CLO004076.106 | *Oryza sativa* | putative protein kinase-like |
| Root/Mannose: whole fraction | CLO004076.106 | *Oryza sativa* | putative protein kinase-like |

In summary, the method of the present invention identified four known proteins from rice that are lectins for mannose or N-acetyl glucosamine. The fact that these known lectins from rice were identified is proof that the method of the invention works as expected to isolate lectins. Additionally, the invention provides a high throughput method for ascribing functions to proteins isolated by this method. As shown in Tables 2 and 3 proteins having no known function can be assigned a function using the methods described herein.

Isolating proteins on the basis of their functional interaction with carbohydrate resins, in combination with proteomics technology, enables one to survey the whole or partial complement of lectin type proteins present in a specific species, tissue, or cell type. It is interesting to note also that the method is clearly capable of identifying proteins that are expressed at low levels in tissues or cells. Lectins as a group represent up to 1% of all proteins in a cell. Because the method described above isolated four specific examples of less than 1% of all proteins, it is clearly useful for identifying proteins expressed at very low levels as well as proteins expressed at higher levels.

Example 5 provides a high-throughput embodiment that uses the MudPIT technique.

Example 5
Identification of Sugar Binding Proteins from Rice Leaf Cells Using Affinity Purification in Tandem with MudPIT Rice protein extracts are prepared from rice leaf as in Example 1. The extracts are applied to the N-Acetyl-D-glucosamine column and isolated as in Example 2. The eluted proteins are dialyzed against 100 mM ammonium bicarbonate pH 8.0. The proteins are treated with trypsin at 37° C. for 3 hours. The peptides are then acidified and subjected MudPIT chromatography and MS (see United States Provisional Application No. 60/305,231, filed Jul. 13, 2001 and Washburn et al. Nature Biotechnology, Vol. 19, March 2001, pages 242–247, the disclosures of which are incorporated herein by reference in their entireties. In brief, the peptide samples loaded onto a two-dimensional HPLC column using an autosampler. The first column dimension contains an anion exchange resin. The second dimension, which is immediately adjacent to the first, contains a reverse phase resin. The eluant from the HPLC column is eluted directly into the electrospray ionization source of a ThermoFinnigan LCQ-Deca ion trap mass spectrometer. Spectra obtained by tandem MS are analyzed using SEQUEST software as described in Example 3.

In Example 6, the method is used to identify metal binding proteins from liver cells.

Example 6
Investigation of Host/Parasite Interactions by Functional Affinity Chromatography A single-cell parasitic microorganism, such as *E. coli* (causative agent of severe food poisoning) or *Plasmodium falciparum* (causative agent of malaria), is harvested from culture and resuspended in isotonic buffer. A small amount of trypsin is added and the culture flask is shaken at 37° C. for 1–3 hours. This causes release of only peptides from proteins which are present and accessible on the cell surface, and therefore directly implicated in cell:cell interactions. The integrity of the cells can be monitored by high-resolution microscopy to ensure that no lysis of cells has occurred. These released peptides are then concentrated from the culture supernatant and identified by LC-MS/MS. One of more identified peptides are then synthesized and coupled to sepharose resin beads to make parasite-specific cell surface peptide affinity column, using established methods.

Cellular lysates from target organs, tissues and fluids of the host organism for th parasites (i.e. humans) are then prepared. Each lysate is passed over the parasite cell surface peptide column, and the bound fraction is eluted using high pH or salt concentration. These eluate fractions are then subjected to protein identification analysis using one or both of two different methods. First, the eluates are fractionated on one-dimensional SDS-PAGE gels, and stained protein bands are excised, digested with trypsin and the resulting peptide mixture is subjected to LC-MS/MS analysis to identify the proteins in the bands. Secondly, the eluates are dialyzed against 100 mM ammonium bicarbonate, subjected to trypsin digestion, and the whole mixture is then subjected to analysis by two-dimensional LC-LC-MS/MS to identify all of the proteins.

The identification of proteins from either of these two experiments provides direct functional information, as they are by definition proteins which are directly involved in the interaction of the parasite with the host cell.

In Example 7, the method is used to identify extracellular matrix proteins in animal cells.

Example 7
Identification of Extracellular Matrix Proteins using Functional Proteomics The primary extracellular matrix (ECM) binding domain for animal cells consist of the amino acid sequence Arg-Gly-Asp (RGD). This binding domain is found in all of the major protein components of the ECM (e.g., laminin, fibronectin, collagen, and elastin) and is specific for interaction with ECM related proteins such as integrins, P-selectins, and adherins.

The RGD peptide, plus several amino acids to serve as a spacer domain (e.g., GSG) is synthesized and coupled to sepharose beads using established methods. Tissue culture cells, for example from a Chinese Hamster Ovary (CHO) cell line, are grown to confluence, harvested into lysis buffer, and separated into soluble and membrane fractions using established methods. These lysis fractions are then diluted into appropriate binding buffer and applied to the cell surface peptide affinity column prepared above. After extensive washing, bound proteins are eluted with an excess of RGD peptide, or by changing to a high pH buffer.

These eluate fractions are then subjected to protein identification analysis using one or both of two different methods. First, the eluates are fractionated on one-dimensional SDS-PAGE gels, and stained protein bands are excised, digested with trypsin and the resulting peptide mixture is subjected to LC-MS/MS analysis to identify the proteins in the bands. Second, the eluates are dialyzed against 100 mM ammonium bicarbonate, subjected to trypsin digestion, and the whole mixture is then subjected to analysis by two-dimensional LC-LC-MS/MS to identify all of the proteins.

The identification of proteins from either of these two experiments provides direct functional information, as they are by definition proteins that are directly involved in the interaction of the cell surface with the extracellular matrix. These interactions are clinically relevant because they are known to undergo changes in pathological states such as apoptosis and metastasis.

In Example 8, the use modifications to protein isolation using functional affinity chromatography are described.

Example 8
Improvements in Affinity Chromatography-Related Techniques to Verify the Binding Specificity of Isolated Proteins The following example provides competition studies to show the specificity of the proteins identified by the functional affinity chromatography. Capture of proteins on an affinity column serves to substantially enrich the concentration of those proteins that are able to specifically bind to the column, while allowing non-specific proteins to be washed away. These bound proteins may then be eluted in a very small volume. Elution is generally accomplished by either changing the buffer to effect a sharp change in pH, or, under more physiological conditions, by addition of a high concentration of competing molecule, for example by loading a high concentration of mannose over a mannose column. Following elution from a particular affinity matrix, the eluant may then be purified further to remove excess salt and or sugar residues. This step will facilitate both downstream gel purification, and further concentration of the eluted sample if necessary. Buffer exchange and concentration may be accomplished separately, for example by dialysis followed by centrifugation through a molecular weight cutoff membrane, or simultaneously, for example by addition of an appropriate buffer during concentration on a pressure-driven stirred cell concentrator. In some cases, for example with samples eluted using lower competitive molecule concentrations, or with samples that are already sufficiently concentrated, these preliminary steps are unnecessary, and the eluant may be run directly onto a one-dimensional or two-dimensional gel, and hence separated from excess salt and/or sugar molecules, or other small contaminants. In each of the examples shown here, proteins eluted from carbohydrate columns have been buffer exchanged and concentrated, then run over a one-dimensional gel for further purification.

Since different proteins may bind to a column with differing affinities, bound protein samples are often eluted over a gradient of increasing concentration of the competing molecule. Incubating the column with increasing concentrations of the competing molecule during binding successively decreases the amounts of specifically bound molecules present in the eluant, while leaving unchanged the concentration of those proteins that are not specifically associated with the resin. This technique is well established in the literature (Lin C. C., et al., *J. Am. Chem. Soc.* 2002, the disclosure of which is incorporated herein by reference in its entirety) as a way of validating the specificity of eluted proteins for the column in question. In the example below, we demonstrate that several bands present in the eluant from an alpha-D-mannose-agarose column can be competed away through the addition of increasing concentrations of free mannose. Downstream identification of these proteins by LC-MS/MS bears out that they are in fact, highly likely to specifically bind mannose.

Figure 4:
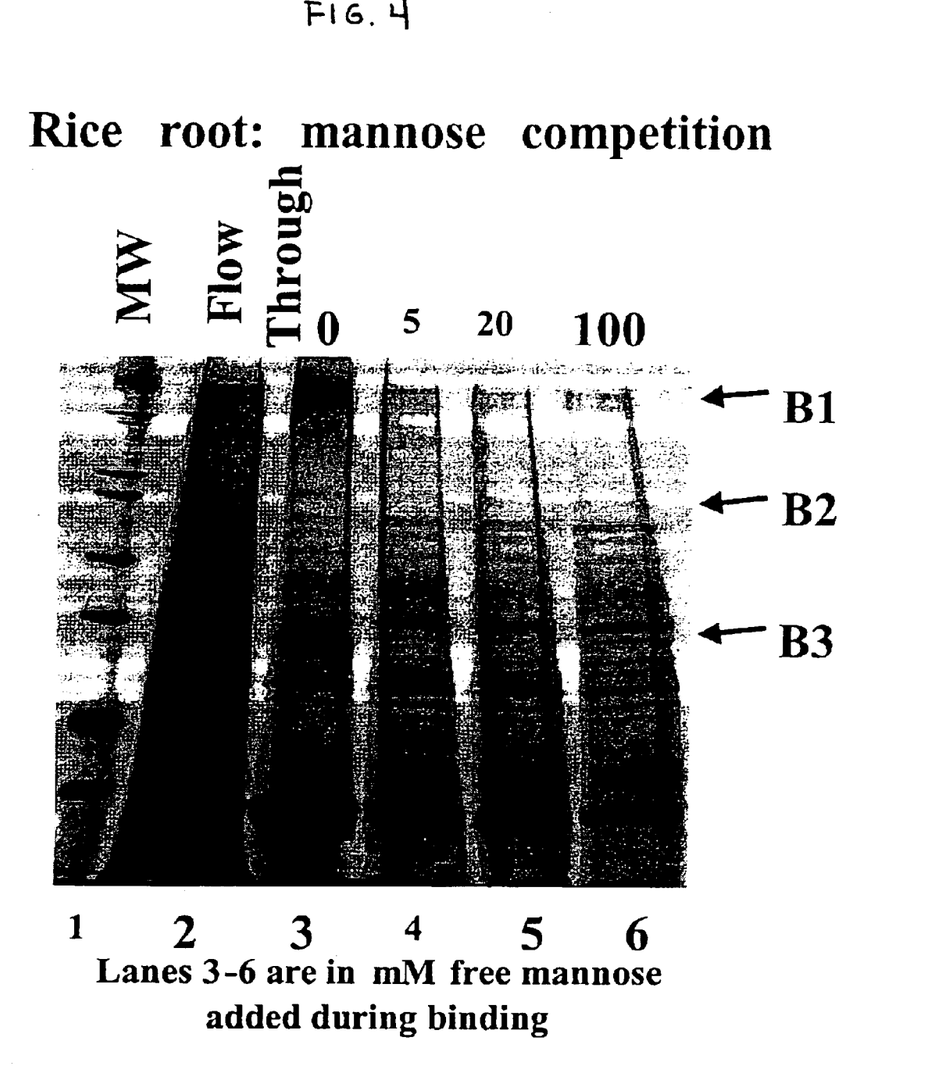
FIG. 4 depicts an SDS polyacrylamide gel showing the effect of including various concentrations of mannose during the binding of rice root extract to a mannose-agarose affinity column.

In particular, an alpha-D-mannose column was incubated with increasing millimolar levels of free mannose during rice root extract binding. After washing with several column volumes worth of equilibration buffer, bound proteins were eluted with 500 mM free mannose. FIG. 4 shows that binding of several protein bands (B1–B3) was successively decreased in the eluant as the concentrations of free mannose during binding increased from 0 mM (lane 3) to 5 mM (lane 4) to 20 mM (lane 5) to 100 mM (lane 6). In particular, FIG. 4 shows that rice citrase (B1), mannose binding jasmonate-induced protein (B2) and rice peroxidase (B3) are effectively competed from binding with the affinity resin as the free mannose concentration during incubation is increased.

In Example 9, functional affinity chromatography coupled with mass spectrometry is used to identify proteins that interact small molecules that are isolated from a combinatorial chemical library.

Example 9

Identification of Proteins which Interact with a Small Molecule Isolated From a Combichem Library Combichem libraries are used to identify and isolate small molecules which might be useful for the treatment of a variety of disease states, such as cancer. In this example, a molecule is identified which is useful in the treatment of malignant melanoma. The molecule is used to produce an affinity column. A malignant melanoma cell is used and the proteome isolated and treated as in Example 7 except a small molecule affinity column is used. Any proteins identified are those which bind to and interact with the small molecule.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Similarly, the various features and steps discussed above, as well as other known equivalents for each such feature or step, can be mixed and matched by one of ordinary skill in this art to perform methods in accordance with principles described herein.

Although the invention has been disclosed in the context of certain embodiments and examples, it will be understood by those skills in the art that the invention extends beyond the specifically disclosed embodiments to other alternative embodiments and/or uses and obvious modifications and equivalents thereof. Accordingly, the invention is not intended to be limited by the specific disclosures of preferred embodiments herein, but instead by reference to claims attached hereto.

What is claimed is:

1. A method of ascribing a function to a protein, said method comprising:
   applying a composition comprising at least one protein to a functional affinity column comprising a ligand, wherein binding of a protein to said ligand is indicative of a function of said bound protein wherein the ligand is a carbohydrate that binds lectins in rice;
   eluting said bound protein from said functional affinity column;
   preparing said eluted protein for mass spectrometry;
   analyzing at least a portion of said eluted protein by mass spectrometry thereby producing spectral information;
   identifying said eluted protein by matching said spectral information with a theoretical mass spectrum of a protein having a known sequence; and
   ascribing a function to said identified protein based on the functional affinity chromatographic behavior of said identified protein.

2. The method of claim 1, wherein preparing said eluted protein for mass spectrometry comprises subjecting said eluted protein to proteolysis and one or more dimensional chromatography.

3. The method of claim 2, wherein said one or more dimensional chromatography is performed using a high performance liquid chromatography column comprising a strong anion exchange resin followed by a reverse phase resin.

4. The method of claim 1, wherein said composition is a protein extract.

5. The method of claim 4, wherein said protein extract is from a tissue or cell.

6. The method of claim 4, wherein said protein extract is fractionated prior to application to said functional affinity column.

7. The method of claim 1, wherein said carbohydrate is N-acetyl-D-glucosamine or N-acetyl-D-galactosamine.

8. The method of claim 1, wherein said bound protein is eluted from said functional affinity column in a single step.

9. The method of claim 1, wherein said bound protein is eluted from said functional affinity column using a stepwise or continuous gradient.

10. The method of claim 1, wherein said mass spectrometry is tandem mass spectrometry.

11. The method of claim 1, wherein the sequence of said protein having a known sequence is present in a database.

12. The method of claim 11, wherein said protein having a known sequence has an unidentified function.

* * * * *